United States Patent [19]

Reiffenrath et al.

[11] Patent Number: 5,084,204
[45] Date of Patent: Jan. 28, 1992

[54] NAPHTHYLACETYLENES

[75] Inventors: Volker Reiffenrath, Rossdorf; Joachim Krause, Dieburg; Georg Weber, Erzhausen, all of Fed. Rep. of Germany

[73] Assignee: Merck Patent Gesellschaft mit Beschrankter Haftung, Darmstadt, Fed. Rep. of Germany

[21] Appl. No.: 269,327

[22] Filed: Nov. 10, 1988

[30] Foreign Application Priority Data

Nov. 11, 1987 [DE] Fed. Rep. of Germany ....... 3738288

[51] Int. Cl.$^5$ .................... C09K 19/32; C07D 239/02; C07C 255/00
[52] U.S. Cl. .................... 252/299.62; 252/299.01; 252/299.6; 544/298; 544/334; 544/336; 544/408; 544/409; 546/290; 546/298; 546/303; 546/314; 546/326; 558/260; 558/270; 558/428; 359/103
[58] Field of Search ..................... 252/299.61, 299.62, 252/299.63, 299.66; 544/298, 334, 408, 409; 546/290, 298, 303, 314, 326; 558/260, 270, 428; 350/350 R

[56] References Cited

U.S. PATENT DOCUMENTS

| | | | |
|---|---|---|---|
| 4,528,114 | 7/1985 | Petrzilka | 252/299.6 |
| 4,680,137 | 7/1987 | Isoyama et al. | 252/299.62 |
| 4,921,632 | 5/1990 | Nakamura et al. | 252/299.1 |

FOREIGN PATENT DOCUMENTS 0284261 9/1988 European Pat. Off. .
3434946 4/1986 Fed. Rep. of Germany .

OTHER PUBLICATIONS

Flussige Kristalle in Tabellen II VEB, Leipzig, 1984.

*Primary Examiner*—John S. Maples
*Assistant Examiner*—Richard Treanor
*Attorney, Agent, or Firm*—Millen, White & Zelano

[57] ABSTRACT

Naphthylacetylenes of the formula I $$R^1-(A^1-Z^1)_m-A^2-C\equiv C-A^3-(Z^2-A^4)_n-R^2 \qquad I$$

in which $R^1$, $A^1$, $Z^1$, m, $A^2$, $A^3$, $Z^2$, $A^4$, n and $R^2$ have the meanings described herein, are suitable as components of liquid crystal phases.

13 Claims, No Drawings

NAPHTHYLACETYLENES

The invention relates to naphthylacetylenes useful as components of liquid crystal phases.

SUMMARY OF THE INVENTION

An object of the invention is to provide new stable liquid crystal or mesogenic compounds which are suitable as components of liquid crystal phases.

Upon further study of the specification and appended claims, further objects and advantages of this invention will become apparent to those skilled in the art.

These objects are achieved by the provision of the compounds of the formula I.

$$R^1-(A^1-Z^1)_m-A^2-C\equiv C-A^3-(Z^2-A^4)_n-R^2 \quad I$$

in which $R^1$ and $R^2$ are in each case independently of one another an alkyl group or polyfluoroalkyl group having up to 15 C atoms, in which one or more CH groups or $CF_2$ groups respectively can also be replaced by —O—, —S—, —CO—, —O—CO—, —O—COO—, —CO—O—, —C≡C—, —CH═CH—, —CH-halogen- and/or —CHCN—, where two heteroatoms are not directly connected with one another, and one of the radicals $R^1$ and $R^2$ can also be H, halogen, CN or NCS, $A^1$ and $A^4$ in each case independently of one another are a (a) 2,6-naphthylene radical, (b) 1,2,3,4-tetrahydro-2,6-naphthylene radical, (c) 1,4-phenylene radical, in which one or more CH groups can also be replaced by N, (d) 1,4-cyclohexylene radical, in which one or two non-adjacent $CH_2$ groups can also be replaced by —O— and/or —S—, or e) radical from the group comprising 1,4-cyclohexenylene, 1,4-cyclohexadienylene or 1,4-bicyclo(2.2.2)-octylene, where these radicals a)–e) can be substituted once or more than once by halogen, cyano and/or $CH_3$, $Z^1$ and $Z^2$ are in each case independently of one another —CO—O—, —O—CO—, —CH$_2$O—, —OCH$_2$—, CH$_2$CH$_2$—, —C≡C— or a single bond m and n are in each case independently of one another 0 or 1, and $A^2$ and $A^3$ are in each case independently of one another (a) 2,6-naphthylene radical, (b) 1,2,3,4-tetrahydro-2,6-naphthylene radical, (c) 1,4-phenylene radical, in which one or more CH groups can also be replaced by N, (d) 1,4-cyclohexylene radical, or (e) radical from the group comprising 1,4-cyclohexenylene, 1,4-cyclohexadienylene or 1,4-bicyclo(2.2.2)-octylene, where these radicals a)–e) can be substituted one or more times by halogen, cyano and/or $CH_3$, with the proviso that at least one of the groups $A^1$, $A^2$, $A^3$ or $A^4$ is 2,6-naphthylene or 1,2,3,4-tetrahydro-2,6-naphthylene.

For simplicity, in the following Phe is a 1,4-phenylene group which is unsubstituted or substituted one or more times by halogen, cyano and/or $CH_3$, Nap is a 2,6-naphthylene group, Tet is a 1,2,3,4-tetrahydro-2,6-naphthylene group, Cyc is a 1,4-cyclohexylene group, Che is a 1,4-cyclohexenylene group, Cha is 1,4-cyclohexadienylene group, Dio is a 1,3-dioxane-2,5-diyl group, Dit is a 1,3-dithiane-2,5-diyl group, Pyd is a pyridine-2,5-diyl group, Pyr is a pyrimidine-2,5-diyl group and Bco is 1,4-bicyclo(2.2.2)octylene group.

The compounds of the formula I can be used as components of liquid crystal phases, in particular for displays which are based on the principle of the twisted cell, the guest-host effect, the effect of the deformation of aligned phases or the effect of dynamic scattering.

Compounds of the formula I are preferably also suitable for use as components in liquid crystal phases for displays which are based on the ECB effect.

It has been found that the compounds of the formula I are particularly suitable as components of liquid crystal phases In particular, stable liquid crystal phases having relatively high optical anisotropy can be prepared with their aid. The substances of the formula I are therefore also suitable for use in mixtures for ECB effects.

The ECB effect (electrically controlled birefringence) or else DAP effect (deformation of aligned phases) was described for the first time in 1971 (M. F. Schieckel and K. Fahrenschon, "Deformation of nematic liquid crystals with vertical orientation in electrical fields", Appl. Phys. Lett. 19 (1971), 3912). Works from J. F. Kahn (Appl. Phys. Lett. 20 (1972), 1193) and G. Labrunie and J. Robert (J. Appl. Phys. 44 (1973), 4869) followed.

The works of J. Robert and F. Clerc (SID 80 Digest Techn. Papers (1980), 30), J. Duchene (Displays 7 (1986), 3) and Schad (SID 82 Digest Technical Papers (1982), 244) have indicated that liquid crystal phases must have high values for the ratio of the elastic constants $K_3/K_1$, high values for optical anisotropy $\Delta n$ and negative values for dielectric anisotropy $\Delta\epsilon$, in order to be able to be employed for highly informative display elements based on the ECB effect.

Electrooptical display elements based on the ECB effect have a homeotropic edge orientation, that is to say the liquid crystal phase has a negative dielectric anisotropy.

It has surprisingly been shown that the addition of compounds of the formula I gives liquid crystal phases which excellently fulfil the abovementioned criteria.

By the preparation of the compounds of the formula I, the range of liquid crystal substances which are suitable for the preparation of nematic mixtures under different commercial application standpoints is additionally quite generally considerably widened.

The compounds of the formula I have a wide range of application. Depending on the selection of the substituents, these compounds can be used as base materials from which liquid crystal phases are predominantly composed; however, compounds of the formula I can also be added to liquid crystal base materials from other classes of compound in order, for example, to optimize the dielectric and/or optical anisotropy of such a dielectric. The compounds of the formula I are furthermore suitable as intermediates for the preparation of other substances which can be used as constituents of liquid crystal phases.

The compounds of the formula I are colorless in the pure state and form liquid crystal mesophases in a temperature range which is favorably placed for electrooptical use. They are very stable chemically, thermally and towards light.

The invention therefore relates to the compounds of the formula (I) and the use of these compounds as components of liquid crystal phases. The invention furthermore relates to liquid crystal phases containing at least one compound of the formula I and liquid crystal display elements which contain phases of this type.

Above and below, $R^1$, $A^1$, $Z^1$, m, $A^2$, $A^3$, $Z^2$, $A^4$, n and $R^2$ have the meaning indicated, unless expressly stated otherwise.

The compounds of the formula I accordingly include compounds of the part formulae Ia (with two ring systems), Ib to Ie (with three ring systems) and If to Ii (with four ring systems):

$R^1$—$A^2$—C≡C—$A^3$—$R^2$     Ia $R^1$—$A^1$—$A^2$—C≡C—$A^3$—$R^2$     Ib $R^1$—$A^1$—$Z^1$—$A^2$—C≡C—$A^3$—$R^2$     Ic $R^1$—$A^2$—C≡C—$A^3$—$A^4$—$R^2$     Id $R^1$—$A^2$—C≡C—$A^3$$Z^2$—$A^4$—$R^2$     Ie $R^1$—$A^1$—$A^2$—C≡C—$A^3$—$A^4$—$R^2$     If $R^1$—$A^1$—$A^2$—C≡C—$A^3$—$A^4$—$R^2$     Ig $R^1$—$A^1$—$A^2$C≡C—$A^3$—$Z^2$—$A^4$—$R^2$     Ih $R^1$—$A^1$—$Z^1$—$A^2$—C≡C—$A^3$—$Z^2$—$A^4$—$R^2$     Ii

Among these, those compounds of the formulae Ia, Ib or Id and Ic or Ie are particularly preferred.

The preferred compounds of the part formula Ia include those of the part formulae Iaa to Iag:

$R^1$—Nap—C≡C—Phe—$R^2$     Iaa $R^1$—Nap—C≡C—Cyc—$R^2$     Iab $R^1$—Nap—C≡C—Che—$R^2$     Iac $R^1$—Nap—C≡C—Cha—$R^2$     Iad $R^1$—Nap—C≡C—Pyd—$R^2$     Iae $R^1$—Nap—C≡C—Pyr—$R^2$     Iaf $R^1$—Tet—C≡C—Phe—$R^2$     Iag

Among these, those compounds of the formulae Iaa and Iab are particularly preferred.

The preferred compounds of the part formulae Ib and Id include those of the part formulae Iba to Ibo:

$R^1$—Nap—Phe—C≡C—Phe—$R^2$     Iba $R^1$—Phe—Nap—C≡C—Phe—$R^2$     Ibb $R^1$—Phe—Phe—C≡C—Nap—$R^2$     Ibc $R^1$—Nap—C≡C—Phe—Cyc—$R^2$     Ibd $R^1$—Nap—C≡C—Phe—Pyd—$R^2$     Ibe $R^1$—Cyc—C≡C—Nap—Phe—$R^2$     Ibf $R^1$—Nap—C≡C—Cyc—Cyc—$R^2$     Ibg $R^1$—Nap—C≡C—Phe—Pyr—$R^2$     Ibh $R^1$—Dio—Cyc—C≡C—Nap—$R^2$     Ibi $R^1$—Nap—Phe—C≡C—Che—$R^2$     Ibj $R^1$—Phe—Nap—C≡C—Pyd—$R^2$     Ibk $R^1$—Cyc—Nap—C≡C—Cyc—$R^2$     Ibl $R^1$—Tet—C≡C—Phe—Phe—$R^2$     Ibm $R^1$—Tet—C≡C—Phe—Pyr—$R^2$     Ibn $R^1$—Tet—C≡C—Phe—Pyr—$R^2$     Ibo

The preferred compounds of the part formulae Ic and Ie include those of the part formulae Ica to Icj:

$R^1$—Nap—C≡C—$A^3$—$CH_2O$—$A^4$—$R^2$     Ica $R^1$—$A^1$—$CH_2O$—$A^2$—C≡C—Nap—$R^2$     Icb $R^1$—$A^1$—$CH_2CH_2$—$A^2$—C≡C—Nap—$R^2$     Icc $R^1$—$A^1$—$CH_2CH_2$—Nap—C≡C—$A^3$—$R^2$     Icd $R^1$—Nap—C≡C—$A^3$—C≡C—$A^4$—$R^2$     Ice $R^1$—Nap—C≡C—$A^3$—COO—$A^4$—$R^2$     Icf $R^1$—Nap—C≡C—$A^3$—OCO—$A^4$—$R^2$     Icg $R^1$—$A^1$—COO—Nap—C≡C—$A^3$—$R^2$     Ich $R^1$—$A^2$—C≡C—$A^3$—$Z^2$—Nap—$R^2$     Ici $R^1$—Tet—C≡C—$A^3$—$Z^2$—$A^4$—$R^2$     Icj

The preferred compounds of the part formulae If, Ig, Ih and Ii include those of the part formulae Ifa to Ifh:

$R^1$—Nap—$A^2$—C≡C—$A^3$—$A^4$—$R^2$     Ifa $R^1$—$A^1$—Nap—C≡C—$A^3$—$A^4$—$R^2$     Ifb $R^1$—$A^1$—$A^2$—C≡C—$A^3$—$Z^2$—Nap—$R^2$     Ifc $R^1$—$A^1$—$A^2$—C≡C—Nap—$Z^2$—$A^4$—$R^2$     Ifd $R^1$—Nap—$Z^1$—$A^2$—C≡C—$A^3$—$Z^2$—$A^4$—$R^2$     Ife $R^1$—$A^1$—$Z^1$—Nap—C≡C—$A^3$—$Z^2$—$A^4$—$R^2$     Iff $R^1$—Tet—$A^2$—C≡C—$A^3$—$A^4$—$R^2$     Ifg $R^1$—$A^1$—$Z^1$—Tet—C≡C—$A^3$—$Z^2$—$A^4$—$R^2$     Ifh $R^1$ and $R^2$ in the formulae above and below preferably have 2–10 C atoms, in particular 3–7 C atoms. In $R^1$ and $R^2$, one or two —$CH_2$— or —$CF_2$— groups can also be replaced. Preferably, only one —$CH_2$— group is replaced by —O—, —CO—, —C≡C—, —S—, —CH=CH—, —CH—halogen— or —CHCN—, in particular by —O—, —CO— or —C≡C—.

In the formulae above and below, $R^1$ and $R^2$ are preferably alkyl, alkoxy or another oxaalkyl group, and furthermore also alkyl groups in which one or more $CH_2$ groups can be replaced by a grouping selected from the group comprising —O—, —O—CO—, —C≡C—, —CH=CH—, —CH-halogen- and —CH-CN— or else by a combination of two suitable groupings, where two hetero atoms are not directly connected to one another.

One of the radicals $R^1$ and $R^2$ is preferably also halogen or CN. Halogen is F, Cl or Br, preferably F. If none of the radicals $R^1$ and $R^2$ are halogen or CN, then $R^1$ and $R^2$ together preferably have 4–16 C atoms, in particular 4–10 C atoms.

$A^1$ and $A^4$ are preferably Cyc, Phe or Nap, and furthermore also Pyd, Tet, Pyr or Che.

$A^2$ and $A^3$ are preferably Cyc, Phe or, particularly preferably, Nap. Furthermore, Pyd, Tet, Che or Pyr are also preferred.

Furthermore, compounds of the formula I in which one of the groups $A^1$, $A^2$, $A^3$ or $A^4$ is 2,6-naphthylene are preferred.

Furthermore, compounds of the formula I which contain a substituted 1,4-phenylene group are preferred. In this case, monosubstitution by F, Cl or CN is preferred, in particular by fluorine.

$Z^1$ and $Z^2$ are preferably a single bond or a —CH$_2$CH$_2$— group. —O—CO— or —CO—O— groups are of secondary preference. Furthermore, $Z^1$ and $Z^2$ are also preferably —CH$_2$O—, —OCH$_2$— or —C≡C—.

m and n are in each case independently of one another 0 or 1, preferably 0.

(m+n) is 0, 1 or 2, preferably 0 or 1.

If $R^1$ and/or $R^2$ are alkyl radicals in which one ("alkoxy" or "oxaalkyl") or two ("alkoxyalkoxy" or "dioxaalkyl") non-adjacent CH$_2$ groups can also be replaced by O atoms, then they can be straight-chain or branched. Preferably, they are straight-chain, have 2, 3, 4, 5, 6 or 7 C atoms and are therefore preferably ethyl, propyl, butyl, pentyl, hexyl, heptyl, ethoxy, propoxy, butoxy, pentoxy, hexoxy, heptoxy, 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, and furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy, tetradecoxy, pentadecoxy, 2-, 3-, 4-, 5-, 6- or 7-oxaoctyl, 2-, 3-, 4-, 5-, 6-, 7- or 8-oxanonyl, 2-, 3-, 4—, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl.

Compounds of the formula I having branched end groups can occasionally be of significance on account of a better solubility in the customary liquid crystal base materials, but in particular as chiral doping substances if they are optically active.

Branched groups of this type as a rule contain not more than one chain branching. Preferred branched radicals for $R^1$ and/or $R^2$ are then isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy (=2-octyloxy), 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

In compounds with branched end groups, formula I includes both the optical antipodes and racemates and also their mixtures.

Among the compounds of the formula I and their subformulae, those are preferred in which at least one of the radicals contained therein has one of the preferred meanings indicated.

Particularly preferred smaller groups of compounds are those of the formulae 1 to 17:

| | |
|---|---|
| Alkyl—Nap—C≡C—Phe—Alkyl | 1 |
| Alkoxy—Nap—C≡C—Phe—Alkyl | 2 |
| Alkyl—Nap—C≡C—Cyc—Alkyl | 3 |
| Alkoxy—Nap—C≡C—Cyc—Alkyl | 4 |
| Alkoxy—Nap—C≡C—Pyd—Alkyl | 5 |
| Alkyl—Nap—C≡C—Pyr—Alkyl | 6 |
| Alkoxy—Nap—C≡C—Phe—Phe—Alkyl | 7 |
| Alkoxy—Nap—C≡C—Phe—Cyc—Alkyl | 8 |
| Alkyl—Nap—C≡C—Phe—Pyd—Alkoxy | 9 |
| Alkoxy—Nap—C≡C—Cyc—Cyc—Alkyl | 10 |
| Alkyl—Phe—Nap—C≡C—Phe—Alkoxy | 11 |
| Alkoxy—Nap—C≡C—Phe—OCH$_2$—Phe—Alkyl | 12 |
| Alkoxy—Nap—C≡C—Cyc—CH$_2$CH$_2$—Cyc—Alkyl | 13 |
| Alkoxy—Nap—C≡C—Phe—C≡C—Alkyl | 14 |
| Alkoxy—Nap—C≡C—Phe—C≡C—Phe—Alkyl | 15 |
| Alkyl—Nap—C≡C—Phe—OCO—Phe—Alkyl | 16 |
| Alkyl—Tet—C≡C—Phe—Alkoxy | 17 |

The 1,2,3,4-tetrahydro-2,6-naphthyl group is preferably connected with the acetylene group in the 6-position.

The 1,4-cyclohexenylene group preferably has the following structures:

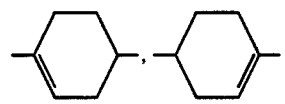

The 1,4-cyclohexadienylene group preferably has the following structure:

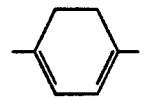

The compounds of the formula I are prepared by methods which are known per se, such as are described in the literature (for example in the standard works such as Houben-Weyl, Methoden der Organischen Chemie [Methods of Organic Chemistry], Georg-Thieme-Verlag, Stuttgart), and in particular under reaction conditions which are known and suitable for the reactions mentioned. In this case, use can also be made of variants which are known per se and which are not mentioned in more detail here.

The starting substances can also be formed, if desired, in situ in such a way that they are not isolated from the reaction mixture, but immediately reacted further to give the compounds of the formula I.

Thus the compounds of the formula I can be prepared by brominating the corresponding stilbenes and subsequently subjecting them to a dehydrohalogenation. In this case, variants of this reaction which are known per se and which are not mentioned in more detail here can be used. The stilbenes can be prepared by reaction of a 4-substituted benzaldehyde with an appropriate phosphorus ylide according to the method of Wittig or by reaction of a 4-substituted phenylethylene with an appropriate bromobenzene derivative according to the method of Heck.

A further possibility for the preparation of the C—C triple bond comprises reacting a compound, which otherwise corresponds to the formula I but contains a —CH$_2$—CO— group in the position of the —C≡C— bond, either with an inorganic acid chloride and then dehydrohalogenating the resulting group —CH$_2$—CCl$_2$— in the presence of the base, or reacting with semicarbazide and selenium dioxide and subsequently converting into the triple bond while warming in the presence of methyllithium.

The possibility furthermore exists of converting an appropriate benzil derivative into the ethyne derivative with hydrazine and subsequently with HgO.

Compounds of the formula I can also be prepared via the coupling of alkynyl-zinc compounds with aryl halides analogously to the process described by A. O. King, E. Negishi, F. J. Villani and A. Silveira in J. Org. Chem. 43 (1978) 358.

Compounds of the formula I can also be prepared by the Fritsch-Buttenberg-Wiechell rearrangement (Ann. 279, 319, 327, 332, 1894), in which 1,1-diaryl-2-halogenoethylenes are rearranged to diarylacetylenes in the presence of strong bases.

Compounds of the formula I can furthermore be prepared from 4-substituted phenyl- or cyclohexylacetylenes and aryl halides in the presence of a palladium catalyst, for example bis(triphenylphosphine)-palladium(II) chloride, and copper(I) iodide (described in Synthesis (1980) 627 or tretrahedron letters 27 (1986) 1171).

Compounds of the formula I are furthermore obtained by adding a compound of the formula HX (hydrogen fluoride, chloride, bromide or cyanide) onto an appropriate cyclohexene derivative.

This addition reaction is carried out, for example, in the presence of an inert solvent, for example a halogenated hydrocarbon such as CH$_2$Cl$_2$ or CHCl$_3$, a nitrile such as acetonitrile or an amide such as dimethylformamide (DMF) at temperatures between −10° and +150° and pressures between 1 and 100 bar. Addition of catalysts can be advantageous, for example addition of HCN can be catalyzed by addition of palladium-bis[2,3-0-isopropylidene-2,3-dihydroxy-1,4-bis(diphenylphosphino)-butane].

Esters of the formula I (—CO—O— or —O—CO— groups in R$^1$ and/or R$^2$ and/or Z$^1$ and/or Z$^2$=—CO—O— or —O—CO—) can also be obtained by esterification of appropriate carboxylic acids (or reactive derivatives thereof) with alcohols or phenols (or their reactive derivatives). The esterification of acids with alcohols or phenols can also be carried out using DCC/DMAP (dicyclohexylcarbodiimide/dimethylaminopyridine).

Suitable reactive derivatives of the carboxylic acids mentioned are in particular the acid halides, above all the chlorides and bromides, and furthermore the anhydrides, for example also mixed anhydrides, azides or esters, in particular alkyl esters having 1-4 C atoms in the alkyl group.

Possible reactive derivatives of the alcohols or phenols mentioned are in particular the appropriate metal alcoholates or phenolates. In these, the metal is preferably an alkali metal such as Na or K.

The esterification is advantageously carried out in the presence of an inert solvent. Ethers such as diethyl ether, di-n-butyl ether, THF, dioxane or anisole, ketones such as acetone, butanone or cyclohexanone, amides such as DMF or hexamethylphosphoric triamide, hydrocarbons such as benzene, toluene or xylene, halogenated hydrocarbons such as carbon tetrachloride or tetrachloroethylene and sulfoxides such as dimethyl sulfoxide or sulfolane are particularly well suited. Water-immiscible solvents can at the same time be advantageously used for the removal by azeotropic distillation of the water formed in the esterification. An excess of an organic base, for example pyridine, quinoline or triethylamine can also occasionally be used as solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are complete, as a rule, after 15 minutes to 48 hours.

In detail, the reaction conditions for the esterification depend substantially on the nature of the starting substances used. Thus a free carboxylic acid is as a rule reacted with a free alcohol or phenol in the presence of a strong acid, for example a mineral acid such as hydrochloric acid or sulfuric acid. A preferred reaction procedure is the reaction of an acid anhydride or, in particular, an acid chloride with an alcohol, preferably in a basic medium, alkali metal hydroxides such as sodium hydroxide or potassium hydroxide, alkali metal carbonates or hydrogen carbonates such as sodium carbonate, sodium hydrogen carbonate, potassium carbonate or potassium hydrogen carbonate, alkali metal acetates such as sodium acetate or potassium acetate, alkaline earth metal hydroxides such as calcium hydroxide or organic bases such as triethylamine, pyridine, lutidine, collidine or quinoline being particularly important. An additional preferred embodiment of the esterification initially comprises converting the alcohol or the phenol into the sodium alcoholate or potassium alcoholate or sodium phenolate or potassium phenolate, for example by treatment with ethanolic sodium hydroxide solution or potassium hydroxide solution, isolating the product and suspending in acetone or diethyl ether together with sodium hydrogen carbonate or potassium carbonate while stirring and adding a solution of the acid chloride or anhydride in diethyl ether, acetone or DMF to this suspension, preferably at temperatures between about −25° and +20°.

Dioxane derivatives or dithiane derivatives of the formula I (in which one of the groups A$^1$, A$^2$, A$^3$ and/or A$^4$ is a 1,3-dioxane-2,5-diyl group or 1,3-dithiane-2,5-diyl group) are preferably prepared by reaction of an appropriate aldehyde (or one of its reactive derivatives) with an appropriate 1,3-diol (or one of its reactive derivatives) or an appropriate 1,3-dithiol, preferably in the presence of an inert solvent such as benzene or toluene and/or a catalyst, for example a strong acid such as sulfuric acid, benzene-or p-toluenesulfonic acid, at temperatures between about 20° and about 150°, preferably between 80° and 120°. Acetals are primarily suitable as reactive derivatives of the starting substances.

The aldehydes and 1,3-diols or 1,3-dithiols mentioned and their reactive derivatives are known in some cases, in some cases they can be prepared without difficulty from compounds which are known from the literature by standard processes of organic chemistry. For example, the aldehydes are obtainable by oxidation of appropriate alcohols or by reduction of appropriate carboxylic acids or their derivatives, the diols are obtainable by reduction of appropriate diesters and the dithiols are obtainable by reaction of appropriate dihalides with NaSH.

In order to prepare nitriles of the formula I (in which $R^1$ or $R^2$ is CN and/or in which $A^3$ and/or $A^1$ and/or $A^2$ and/or $A^4$ is substituted by at least one CN group), appropriate acid amides are dehydrated. The amides are obtainable, for example, from appropriate esters or acid halides by reaction with ammonia. Suitable dehydrating agents are, for example, inorganic acid chlorides such as $SOCl_2$, $PCl_3$, $PCl_5$, $POCl_3$, $SO_2Cl_2$, $COCl_2$ and furthermore $P_2O_5$, $P_2S_5$, $AlCl_3$ (for example as the double compound with NaCl), aromatic sulfonic acids and sulfonyl halides. In this case, the reaction can be carried out in the presence or absence of an inert solvent at temperatures between about 0° and 150°; possible solvents are, for example, bases such as pyridine or triethylamine, aromatic hydrocarbons such as benzene, toluene or xylene or amides such as DMF.

In order to prepare the nitriles of the formula I mentioned previously, appropriate acid halides, preferably the chlorides, also can be reacted with sulfamide, preferably in an inert solvent such as tetramethylene sulfone at temperatures between about 80° and 150°, preferably at 120°. After customary working up, the nitriles can be isolated directly.

Ethers of the formula I are obtainable by etherification of appropriate phenols, the hydroxyl compound preferably being first converted into a corresponding metal derivative, for example by treating with NaH, $NaNH_2$, NaOH, KOH, $Na_2CO_3$ or $K_2CO_3$ into the corresponding alkali metal alcoholate or alkali metal phenolate. This can then be reacted with the appropriate alkyl halide, sulfonate or dialkyl sulfate, preferably in an inert solvent such as acetone, 1,2-dimethoxyethane, DMF or dimethyl sulfoxide or else an excess of aqueous or aqueous-alcoholic NaOH or KOH at temperatures between about 20° and 100°.

The thioethers are prepared by methods which are known per se, such as are described in the literature (for example in the standard works such as Houben-Weyl, Methoden der Organischen Chemie [Methods of Organic Chemistry], Georg-Thieme-Verlag, Stuttgart), and in particular under reaction conditions which are known and suitable for the reactions mentioned. The thioethers are preferably obtained by treatment of appropriate halogen compounds, in which halogen is chlorine, bromine or iodine, with salts of appropriate mercaptans.

These halogen compounds are either known or can be prepared without difficulty in analogy to known compounds by methods which are known per se. Thus, for example, p-substituted halogenobenzene derivatives are accessible by halogenation of the appropriate benzene derivatives. 4-Substituted cyclohexyl halides are obtainable, for example, by reduction of the appropriate 4-substituted cyclohexanones to the 4-substituted cyclohexanols and subsequent substitution by halide.

In the synthesis of the halogen compounds, in principle all methods can be used which are known for the compounds which carry other substituents instead of the halogen. The expert can deduce the necessary synthesis variants by routine methods.

In order to prepare nitriles of the formula I (in which $R^1$ or $R^2$ is CN and/or in which $A^3$ and/or $A^4$ and/or $A^1$ and/or $A^2$ is substituted by at least one CN group), appropriate chlorine or bromine compounds of the formula I can also be reacted with a cyanide, preferably with a metal cyanide such as NaCN, KCN or $Cu_2(CN)_2$, for example in the presence of pyridine in an inert solvent such as DMF or N-methylpyrrolidone at temperatures between 20° and 200°.

The liquid crystal phases according to the invention consist of 2 to 15, preferably 3 to 12 components, among which is at least one compound of the formula I. The other constituents are preferably selected from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenyl cyclohexanes, cyclohexylbiphenyls, cyclohexylcyclohexanes, cyclohexylnaphthalenes, 1,4-bis-cyclohexylbenzenes, 4,4'- bis-cyclohexylbiphenyls, phenyl- or cyclohexylpyrimidines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers and substituted cinnamic acids.

The most important compounds which are possible as constituents of this type of liquid crystal phases can be characterized by the formula IV $$R^6—L—G—E—R^7 \qquad IV$$

in which

L and E are each independently a carbocyclic or heterocyclic ring system from the groups formed from 1,4-disubstituted benzene and cyclohexane rings, 4,4'-disubstituted biphenyl-, phenylcyclohexane- and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

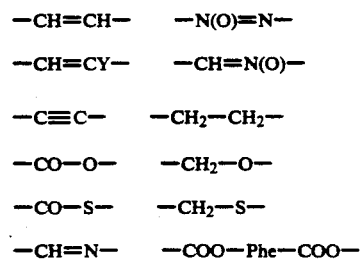

or a C—C single bond,

Y is halogen, preferably chlorine, or —CN, and $R^6$ and $R^7$ are independently alkyl, alkoxy, alkanoyloxy or alkoxycarbonyloxy having up to 18, preferably up to 8, carbon atoms, or one of these radicals is CN, NC, $NO_2$, $CF_3$, F, Cl or Br.

In most of these compounds, $R^6$ and $R^7$ are different from one another, one of these radicals usually being an alkyl or alkoxy group. Other variants of the intended substituents are also common. Many such substances or else mixtures thereof are commercially available. All these substances are obtainable by methods which are known from the literature.

The phases according to the invention contain about 0.1 to 99, preferably 10 to 95%, of one or more compounds of the formula I. Furthermore, liquid crystal phases according to the invention containing 0.1–40, preferably 0.5–30%, of one or more compounds of the formula I are preferred.

The compounds of the formula I can also be used as components of smectic or chirally tilted smectic liquid crystal phases. These phases are preferably chirally tilted smectic liquid crystal phases whose achiral base mixture contains another component with a negative or, according to the amount, a small positive dielectric anisotropy in addition to compounds of the formula I. This (these) additional component(s) of the achiral base mixture can make up 1 to 50%, preferably 10 to 25%, of the base mixture.

The preparation of the phases according to the invention is carried out in a customary manner. As a rule, the components are dissolved in one another, preferably at elevated temperature. By means of suitable additives, the liquid crystal phases according to the invention can be modified in such a way that they can be used in all hitherto disclosed types of liquid crystal display elements.

Additives of this type are known to the expert and are described in detail in the literature. For example, conductive salts, preferably ethyldimethyldodecylammonium 4-hexyloxybenzoate, tetrabutylammonium, tetraphenylborohydride or complex salts of crown ethers (compare, for example, I. Haller et al., Mol. Cryst. Liq. Cryst. Volume 24, pages 249–258 (1973)) can be added to improve the conductivity, dichroic dyestuffs can be added to prepare colored guest-host systems or substances can be added to alter the dielectric anisotropy, the viscosity and/or the orientation of the nematic phases. Substances of this type are described, for example, in DE-OS 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire texts of all applications, patents and publications, if any, cited above and below, and of corresponding German application P 37 38 288.8 (the priority document), are hereby incorporated by reference.

The following examples are intended to illustrate the invention, without limiting it thereto. M.=Melting point, C.=clear point. Above and below, percentage data are percent by weight; all temperatures are indicated in degrees Celsius. "Customary work-up" means: water is added, the mixture is extracted using methylene chloride, the organic phase is separated off, dried and evaporated, and the product is purified by crystallization and/or chromatography.

EXAMPLES

Example 1

(a) 0.2 mol of 2-bromo-6-ethoxynaphthalene are added dropwise in 200 ml of THF to 0.22 mol of magnesium turnings. The mixture is heated to reflux for a further 1 hour and cooled to room temperature, and 0.21 mol of 4-pentylacetophenone in 50 ml of THF are added at 15°–20°.

The mixture is stirred for a further 15 minutes at room temperature, hydrolyzed using saturated $NH_4Cl$ solution and worked up by extraction. After evaporating the extract, 150 ml of 20% $H_2SO_4$ is added to the residue and the mixture is heated to reflux for 1 hour. The reaction mixture is again worked up by extraction. Recrystallization from methanol/ethanol gives 1-(4-pentylphenyl)-1-(6-ethoxy-2-naphthyl)ethene.

(b) 0.112 mol of $Br_2$ is added to 0.112 mol of 1-(4-pentylphenyl)-1-(6-ethoxy-2-naphthyl)ethene in 150 ml of toluene and 100 ml of methanol at about 10°. The reaction mixture is evaporated and the residue is heated at reflux for 4 hours together with 0.4 mol of potassium tert.-butylate and 200 ml of tert.-butanol. After cooling, pouring into water and filtering the product with suction gives, after purification by recrystallization, 1-(4-pentylphenyl)-2-(6-ethoxy-2-naphthyl)-acetylene having M. 110° and C. 157.3°.

The following compounds are prepared analogously:
1-(4-Methylphenyl)-2-(6-ethoxy-2-naphthyl)-acetylene
1-(4-Ethylphenyl)-2-(6-ethoxy-2-naphthyl)-acetylene
1-(4-Propylphenyl)-2-(6-ethoxy-2-naphthyl)-acetylene
1-(4-Butylphenyl)-2-(6-ethoxy-2-naphthyl)-acetylene
1-(4-Hexylphenyl)-2-(6-ethoxy-2-naphthyl)-acetylene
1-(4-Heptylphenyl)-2-(6-ethoxy-2-naphthyl)-acetylene
1-(4-Octylphenyl)-2-(6-ethoxy-2-naphthyl)-acetylene
1-(4-Methoxyphenyl)-2-(6-ethoxy-2-naphthyl)-acetylene
1-(4-Ethoxyphenyl)-2-(6-ethoxy-2-naphthyl)-acetylene
1-(4-Propoxyphenyl)-2-(6-ethoxy-2-naphthyl)-acetylene
1-(4-Butoxyphenyl)-2-(6-ethoxy-2-naphthyl)-acetylene
1-(4-Pentyloxyphenyl)-2-(6-ethoxy-2-naphthyl)-acetylene
1-(4-Hexyloxyphenyl)-2-(6-ethoxy-2-naphthyl)-acetylene
1-(4-Heptyloxyphenyl)-2-(6-ethoxy-2-naphthyl)-acetylene
1-(4-Methylphenyl)-2-(6-methoxy-2-naphthyl)-acetylene
1-(4-Ethylphenyl)-2-(6-methoxy-2-naphthyl)-acetylene
1-(4-Propylphenyl)-2-(6-methoxy-2-naphthyl)-acetylene
1-(4-Butylphenyl)-2-(6-methoxy-2-naphthyl)-acetylene
1-(4-Pentylphenyl)-2-(6-methoxy-2-naphthyl)-acetylene
1-(4-Hexylphenyl)-2-(6-methoxy-2-naphthyl)-acetylene
1-(4-Heptylphenyl)-2-(6-methoxy-2-naphthyl)-acetylene
1-(4-Octylphenyl)-2-(6-methoxy-2-naphthyl)-acetylene
1-(4-Methoxyphenyl)-2-(6-methoxy-2-naphthyl)-acetylene
1-(4-Ethoxyphenyl)-2-(6-methoxy-2-naphthyl)-acetylene
1-(4-Propoxyphenyl)-2-(6-methoxy-2-naphthyl)-acetylene
1-(4-Butoxyphenyl)-2-(6-methoxy-2-naphthyl)-acetylene 1-(4-Pentyloxyphenyl)-2-(6-methoxy-2-naphthyl)-acetylene
1-(4-Hexyloxyphenyl)-2-(6-methoxy-2-naphthyl)-acetylene
1-(4-Heptyloxyphenyl)-2-(6-methoxy-2-naphthyl)-acetylene
1-(4-Methylphenyl)-2-(6-propoxy-2-naphthyl)-acetylene
1-(4-Ethylphenyl)-2-(6-propoxy-2-naphthyl)-acetylene
1-(4-Propylphenyl)-2-(6-propoxy-2-naphthyl)-acetylene
1-(4-Butylphenyl)-2-(6-propoxy-2-naphthyl)-acetylene
1-(4-Pentylphenyl)-2-(6-propoxy-2-naphthyl)-acetylene
1-(4-Hexylphenyl)-2-(6-propoxy-2-naphthyl)-acetylene
1-(4-Heptylphenyl)-2-6-propoxy-2-naphthyl)-acetylene
1-(4-Octylphenyl)-2-(6-propoxy-2-naphthyl)-acetylene
1-(4-Methoxyphenyl)-2-(6-propoxy-2-naphthyl)-acetylene
1-(4-Ethoxyphenyl)-2-(6-propoxy-2-naphthyl)-acetylene
1-(4-Propoxyphenyl)-2-(6-propoxy-2-naphthyl)-acetylene
1-(4-Butoxyphenyl)-2-(6-propoxy-2-naphthyl)-acetylene
1-(4-Pentyloxyphenyl)-2-(6-propoxy-2-naphthyl)-acetylene
1-(4-Hexyloxyphenyl)-2-(6-propoxy-2-naphthyl)-acetylene
1-(4-Heptyloxyphenyl)-2-(6-propoxy-2-naphthyl)-acetylene
1-(4-Methylphenyl)-2-(6-butoxy-2-naphthyl)-acetylene
1-(4-Ethylphenyl)-2-(6-butoxy-2-naphthyl)-acetylene
1-(4-Propylphenyl)-2-(6-butoxy-2-naphthyl)-acetylene
1-(4-Butylphenyl)-2-(6-butoxy-2-naphthyl)-acetylene
1-(4-Pentylphenyl)-2-(6-butoxy-2-naphthyl)-acetylene
1-(4-Hexylphenyl)-2-(6-butoxy-2-naphthyl)-acetylene
1-(4-Heptylphenyl)-2-(6-butoxy-2-naphthyl)-acetylene
1-(4-Octylphenyl)-2-(6-butoxy-2-naphthyl)-acetylene
1-(4-Methoxyphenyl)-2-(6-butoxy-2-naphthyl)-acetylene
1-(4-Ethoxyphenyl)-2-(6-butoxy-2-naphthyl)-acetylene
1-(4-Propoxyphenyl)-2-(6-butoxy-2-naphthyl)-acetylene
1-(4-Butoxyphenyl)-2-(6-butoxy-2-naphthyl)-acetylene
1-(4-Pentyloxyphenyl)-2-(6-butoxy-2-naphthyl)-acetylene
1-(4-Hexyloxyphenyl)-2-(6-butoxy-2-naphthyl)-acetylene
1-(4-Heptyloxyphenyl)-2-(6-butoxy-2-naphthyl)-acetylene
1-(4-Methylphenyl)-2-(6-pentyloxy-2-naphthyl)-acetylene
1-(4-Ethylphenyl)-2-(6-pentyloxy-2-naphthyl)-acetylene
1-(4-Propylphenyl)-2-(6-pentyloxy-2-naphthyl)-acetylene
1-(4-Butylphenyl)-2-(6-pentyloxy-2-naphthyl)-acetylene
1-(4-Pentylphenyl)-2-(6-pentyloxy-2-naphthyl)-acetylene
1-(4-Hexylphenyl)-2-(6-pentyloxy-2-naphthyl)-acetylene
1-(4-Heptylphenyl)-2-(6-pentyloxy-2-naphthyl)-acetylene
1-(4-Octylphenyl)-2-(6-pentyloxy-2-naphthyl)-acetylene
1-(4-Methoxyphenyl)-2-(6-pentyloxy-2-naphthyl)-acetylene
1-(4-Ethoxyphenyl)-2-(6-pentyloxy-2-naphthyl)-acetylene
1-(4-Propoxyphenyl)-2-(6-pentyloxy-2-naphthyl)-acetylene
1-(4-Butoxyphenyl)-2-(6-pentyloxy-2-naphthyl)-acetylene
1-(4-Pentyloxyphenyl)-2-(6-pentyloxy-2-naphthyl)-acetylene
1-(4-Hexyloxyphenyl)-2-(6-pentyloxy-2-naphthyl)-acetylene
1-(4-Heptyloxyphenyl)-2-(6-pentyloxy-2-naphthyl)-acetylene
1-(4-Methylphenyl)-2-(6-hexyloxy-2-naphthyl)-acetylene
1-(4-Ethylphenyl)-2-(6-hexyloxy-2-naphthyl)-acetylene
1-(4-Propylphenyl)-2-(6-hexyloxy-2-naphthyl)-acetylene
1-(4-Butylphenyl)-2-(6-hexyloxy-2-naphthyl)-acetylene
1-(4-Pentylphenyl)-2-(6-hexyloxy-2-naphthyl)-acetylene
1-(4-Hexylphenyl)-2-(6-hexyloxy-2-naphthyl)-acetylene
1-(4-Heptylphenyl)-2-(6-hexyloxy-2-naphthyl)-acetylene
1-(4-Octylphenyl)-2-(6-hexyloxy-2-naphthyl)-acetylene
1-(4-Methoxyphenyl)-2-(6-hexyloxy-2-naphthyl)-acetylene
1-(4-Ethoxyphenyl)-2-(6-hexyloxy-2-naphthyl)-acetylene
1-(4-Propoxyphenyl)-2-(6-hexyloxy-2-naphthyl)-acetylene
1-(4-Butoxyphenyl)-2-(6-hexyloxy-2-naphthyl)-acetylene
1-(4-Pentyloxyphenyl)-2-(6-hexyloxy-2-naphthyl)-acetylene
1-(4-Hexyloxyphenyl)-2-(6-hexyloxy-2-naphthyl)-acetylene
1-(4-Heptyloxyphenyl)-2-(6-hexyloxy-2-naphthyl)-acetylene
1-(4-Methylphenyl)-2-(6-heptyloxy-2-naphthyl)-acetylene
1-(4-Ethylphenyl)-2-(6-heptyloxy-2-naphthyl)-acetylene
1-(4-Propylphenyl)-2-(6-heptyloxy-2-naphthyl)-acetylene
1-(4-Butylphenyl)-2-(6-heptyloxy 2-naphthyl)-acetylene
1-(4-Pentylphenyl)-2-(6-heptyloxy-2-naphthyl)-acetylene
1-(4-Hexylphenyl)-2-(6-heptyloxy-2-naphthyl)-acetylene
1-(4-Heptylphenyl)-2-(6-heptyloxy-2-naphthyl)-acetylene
1-(4-Octylphenyl)-2-(6-heptyloxy-2-naphthyl)-acetylene
1-(4-Methoxyphenyl)-2-(6-heptyloxy-2-naphthyl)-acetylene
1-(4-Ethoxyphenyl)-2-(6-heptyloxy-2-naphthyl)-acetylene
1-(4-Propoxyphenyl)-2-(6-heptyloxy-2-naphthyl)-acetylene
1-(4-Butoxyphenyl)-2-(6-heptyloxy-2-naphthyl)-acetylene
1-(4-Pentyloxyphenyl)-2-(6-heptyloxy-2-naphthyl)-acetylene
1-(4-Hexyloxyphenyl)-2-(6-heptyloxy-2-naphthyl)-acetylene
1-(4-Heptyloxyphenyl)-2-(6-heptyloxy-2-naphthyl)-acetylene
1-(4-Methylphenyl)-2-(6-ethyl-2-naphthyl)-acetylene 1-(4-Ethylphenyl)-2-(6-ethyl-2-naphthyl)-acetylene
1-(4-Propylphenyl)-2-(6-ethyl-2-naphthyl)-acetylene
1-(4-Butylphenyl)-2-(6-ethyl-2-naphthyl)-acetylene
1-(4-Pentylphenyl)-2-(6-ethyl-2-naphthyl)-acetylene
1-(4-Hexylphenyl)-2-(6-ethyl-2-naphthyl)-acetylene
1-(4-Heptylphenyl)-2-(6-ethyl-2-naphthyl)-acetylene
1-(4-Octylphenyl)-2-(6-ethyl-2-naphthyl)-acetylene
1-(4-Methoxyphenyl)-2-(6-ethyl-2-naphthyl)-acetylene
1-(4-Ethoxyphenyl)-2-(6-ethyl-2-naphthyl)-acetylene
1-(4-Propoxyphenyl)-2-(6-ethyl-2-naphthyl)-acetylene
1-(4-Butoxyphenyl)-2-(6-ethyl-2-naphthyl)-acetylene
1-(4-Pentyloxyphenyl)-2-(6-ethyl-2-naphthyl)-acetylene
1-(4-Hexyloxyphenyl)-2-(6-ethyl-2-naphthyl)-acetylene
1-(4-Heptyloxyphenyl)-2-(6-ethyl-2-naphthyl)-acetylene
1-(4-Methylphenyl)-2-(6-propyl-2-naphthyl)-acetylene
1-(4-Ethylphenyl)-2-(6-propyl-2-naphthyl)-acetylene
1-(4-Propylphenyl)-2-(6-propyl-2-naphthyl)-acetylene
1-(4-Butylphenyl)-2-(6-propyl-2-naphthyl)-acetylene
1-(4-Pentylphenyl)-2-(6-propyl-2-naphthyl)-acetylene
1-(4-Hexylphenyl)-2-(6-propyl-2-naphthyl)-acetylene
1-(4-Heptylphenyl)-2-(6-propyl-2-naphthyl)-acetylene
1-(4-Octylphenyl)-2-(6-propyl-2-naphthyl)-acetylene
1-(4-Methoxyphenyl)-2-(6-propyl 2 naphthyl)-acetylene
1-(4-Ethoxyphenyl)-2-(6-propyl-2-naphthyl)-acetylene
1-(4-Propoxyphenyl)-2-(6-propyl-2-naphthyl)-acetylene
1-(4-Butoxyphenyl)-2-(6-propyl-2-naphthyl)-acetylene
1-(4-Pentyloxyphenyl)-2-(6-propyl-2-naphthyl)-acetylene
1-(4-Hexyloxyphenyl)-2-(6-propyl-2-naphthyl)-acetylene
1-(4-Heptyloxyphenyl)-2-(6-propyl-2-naphthyl)-acetylene
1-(4-Methylphenyl)-2-(6-butyl-2-naphthyl)-acetylene
1-(4-Ethylphenyl)-2-(6-butyl-2-naphthyl)-acetylene
1-(4-Propylphenyl)-2-(6-butyl-2-naphthyl)-acetylene
1-(4-Butylphenyl)-2-(6-butyl-2-naphthyl)-acetylene
1-(4-Pentylphenyl)-2-(6-butyl-2-naphthyl)-acetylene
1-(4-Hexylphenyl)-2-(6-butyl-2-naphthyl)-acetylene
1-(4-Heptylphenyl)-2-(6-butyl-2-naphthyl)-acetylene
1-(4-Octylphenyl)-2-(6-butyl-2-naphthyl)-acetylene
1-(4-Methoxyphenyl)-2-(6-butyl-2-naphthyl)-acetylene
1-(4-Ethoxyphenyl)-2-(6-butyl-2-naphthyl)-acetylene
1-(4-Propoxyphenyl)-2-(6-butyl-2-naphthyl)-acetylene
1-(4-Butoxyphenyl)-2-(6-butyl-2-naphthyl)-acetylene
1-(4-Pentyloxyphenyl)-2-(6-butyl-2-naphthyl)-acetylene
1-(4-Hexyloxyphenyl)-2-(6-butyl-2-naphthyl)-acetylene
1-(4-Heptyloxyphenyl)-2-(6-butyl-2-naphthyl)-acetylene
1-(4-Methylphenyl)-2-(6-pentyl-2-naphthyl)-acetylene
1-(4-Ethylphenyl)-2-(6-pentyl-2-naphthyl)-acetylene
1-(4-Propylphenyl)-2-(6-pentyl-2-naphthyl)-acetylene
1-(4-Butylphenyl)-2-(6-pentyl-2-naphthyl)-acetylene
1-(4-Pentylphenyl)-2-(6-pentyl-2-naphthyl)-acetylene
1-(4-Hexylphenyl)-2-(6-pentyl-2-naphthyl)-acetylene
1-(4-Heptylphenyl)-2-(6-pentyl-2-naphthyl)-acetylene
1-(4-Octylphenyl)-2-(6-pentyl-2-naphthyl)-acetylene
1-(4-Methoxyphenyl)-2-(6-pentyl-2-naphthyl)-acetylene
1-(4-Ethoxyphenyl)-2-(6-pentyl-2-naphthyl)-acetylene
1-(4-Propoxyphenyl)-2-(6-pentyl-2-naphthyl)-acetylene
1-(4-Butoxyphenyl)-2-(6-pentyl-2-naphthyl)-acetylene
1-(4-Pentyloxyphenyl)-2-(6-pentyl-2-naphthyl)-acetylene
1-(4-Hexyloxyphenyl)-2-(6-pentyl-2-naphthyl)-acetylene
1-(4-Heptyloxyphenyl)-2-(6-pentyl-2-naphthyl)-acetylene
1-(4-Methylphenyl)-2-(6-hexyl-2-naphthyl)-acetylene
1-(4-Ethylphenyl)-2-(6-hexyl-2-naphthyl)-acetylene
1-(1-Propylphenyl)-2-(6-hexyl-2-naphthyl)-acetylene
1-(4-Butylphenyl)-2-(6-hexyl-2-naphthyl)-acetylene
1-(4-Pentylphenyl)-2-(6-hexyl-2-naphthyl)-acetylene
1-(4-Hexylphenyl)-2-(6-hexyl-2-naphthyl)-acetylene
1-(4-Heptylphenyl)-2-(6-hexyl-2-naphthyl)-acetylene
1-(4-Octylphenyl)-2-(6-hexyl-2-naphthyl)-acetylene
1-(4-Methoxyphenyl)-2-(6-hexyl-2-naphthyl)-acetylene
1-(4-Ethoxyphenyl)-2-(6-hexyl-2-naphthyl)-acetylene
1-(4-Propoxyphenyl)-2-(6-hexyl-2-naphthyl)-acetylene
1-(4-Butoxyphenyl)-2-(6-hexyl-2-naphthyl)-acetylene
1-(4-Pentyloxyphenyl)-2-(6-hexyl-2-naphthyl)-acetylene
1-(4-Hexyloxyphenyl)-2-(6-hexyl-2-naphthyl)-acetylene
1-(4-Heptyloxyphenyl)-2-(6-hexyl-2-naphthyl)-acetylene
1-(4-Methylphenyl)-2-(6-heptyl-2-naphthyl)-acetylene
1-(4-Ethylphenyl)-2-(6-heptyl-2-naphthyl)-acetylene
1-(4-Propylphenyl)-2-(6-heptyl-2-naphthyl)-acetylene
1-(4-Butylphenyl)-2-(6-heptyl-2-naphthyl)-acetylene
1-(4-Pentylphenyl)-2-(6-heptyl-2-naphthyl)-acetylene
1-(4-Hexylphenyl)-2-(6-heptyl-2-naphthyl)-acetylene
1-(4-Heptylphenyl)-2-(6-heptyl-2-naphthyl)-acetylene
1-(4-Octylphenyl)-2-(6-heptyl-2-naphthyl)-acetylene
1-(4-Methoxyphenyl)-2-(6-heptyl-2-naphthyl)-acetylene
1-(4-Ethoxyphenyl)-2-(6-heptyl-2-naphthyl-acetylene
1-(4-Propoxyphenyl)-2-(6-heptyl-2-naphthyl)-acetylene
1-(4-Butoxyphenyl)-2-(6-heptyl-2-naphthyl)-acetylene
1-(4-Pentyloxyphenyl)-2-(6-heptyl-2-naphthyl)-acetylene
1-(4-Hexyloxyphenyl)-2-(6-heptyl-2-naphthyl)-acetylene
1-(4-Heptyloxyphenyl)-2-(6-heptyl-2-naphthyl)-acetylene
1-(4'-Methylbiphenyl-4-yl)-2-(6-methoxy-2-naphthyl)acetylene
1-(4'-Ethylbiphenyl-4-yl)-2-(6-methoxy-2-naphthyl)acetylene
1-(4'-Propylbiphenyl-4-yl)-2-(6-methoxy-2-naphthyl)acetylene
1-(4'-Butylbiphenyl-4-yl)-2-(6-methoxy-2-naphthyl)acetylene
1-(4'-Pentylbiphenyl-4-yl)-2-(6-methoxy-2-naphthyl)acetylene
1-(4'-Hexylbiphenyl-4-yl)-2-(6-methoxy-2-naphthyl)acetylene
1-(4'-Heptylbiphenyl-4-yl)-2-(6-methoxy-2-naphthyl)acetylene
1-(4'-Octylbiphenyl-4-yl)-2-(6-methoxy-2-naphthyl)acetylene
1-(4'-Methoxybiphenyl-4-yl-)-2-(6-methoxy-2-naphthyl)acetylene
1-(4'-Ethoxybiphenyl-4-yl)-2-naphthyl)acetylene
1-(4'-Propoxybiphenyl-4-yl)-2-naphthyl)acetylene
1-(4'-Butoxybiphenyl-4-yl)-2-(6-methoxy-2-naphthyl)acetylene
1-(4'-Pentyloxybiphenyl-4-yl)-2-(6-methoxy-2-naphthyl)acetylene
1-(4'-Hexyloxybiphenyl-4-yl)-2-(6-methoxy-2-naphthyl)acetylene
1-(4'-Heptyloxybiphenyl-4-yl)-2-(6-methoxy-2-naphthyl)acetylene
1-(4'-Methylbiphenyl-4-yl)-2-(6-ethoxy-2-naphthyl)acetylene
1-(4'-Ethylbiphenyl-4-yl)-2-(6-ethoxy-2-naphthyl)acetylene 1-(4'-Propylbiphenyl-4-yl)-2-(6-ethoxy-2-naphthyl)acetylene
1-(4'-Butylbiphenyl-4-yl)-2-(6-ethoxy-2-naphthyl)acetylene
1-(4'-Pentylbiphenyl-4-yl)-2-(6-ethoxy-2 naphthyl)acetylene
1-(4'-Hexylbiphenyl-4-yl)-2-(6-ethoxy-2-naphthyl)acetylene
1-(4'-Heptylbiphenyl-4-yl)-2-(6-ethoxy-2-naphthyl)acetylene
1-(4'-Octylbiphenyl-4-yl)-2-(6-ethoxy-2-naphthyl)acetylene
1-(4'-Methoxybiphenyl-4-yl)-2-(6-ethoxy-2-naphthyl)acetylene
1-(4'-Ethoxybiphenyl-4-yl)-2-(6-ethoxy-2-naphthyl)acetylene
1-(4'-Propoxybiphenyl-4-yl)-2-(6-ethoxy-2-naphthyl)acetylene
1-(4'-Butoxybiphenyl-4-yl)-2-(6-ethoxy-2-naphthyl)acetylene
1-(4'-Pentyloxybiphenyl-4-yl)-2-(6-ethoxy-2-naphthyl)acetylene
1-(4'-Hexyloxybiphenyl-4-yl)-2-(6-ethoxy-2-naphthyl)acetylene
1-(4'-Heptyloxybiphenyl-4-yl)-2-(6-ethoxy-2-naphthyl)acetylene
1-(4'-Methylbiphenyl-4-yl)-2-(6-propoxy-2-naphthyl)acetylene
1-(4'-Ethylbiphenyl-4-yl)-2-(6-propoxy-2-naphthyl)acetylene
1-(4'-Propylbiphenyl-4-yl)-2-(6-propoxy-2-naphthyl)acetylene
1-(4'-Butylbiphenyl-4-yl)-2-(6-propoxy-2-naphthyl)acetylene
1-(4'-Pentylbiphenyl-4-yl)-2-(6-propoxy-2-naphthyl)acetylene
1-(4'-Hexylbiphenyl-4-yl)-2-(6-propoxy-2-naphthyl)acetylene
1-(4'-Heptylbiphenyl-4-yl)-2-(6-propoxy-2-naphthyl)acetylene
1-(4'-Octylbiphenyl-4 yl)-2 (6-propoxy 2-naphthyl)acetylene
1-(4'-Methoxybiphenyl-4-yl)-2-(6-propoxy-2-naphthyl)acetylene
1-(4'-Ethoxybiphenyl-4-yl)-2-(6-propoxy-2-naphthyl)acetylene
1-(4'-Propoxybiphenyl-4-yl)-2-(6-propoxy-2-naphthyl)acetylene
1-(4'-Butoxybiphenyl-4-yl)-2-(6-propoxy-2-naphthyl)acetylene
1-(4'-Pentyloxybiphenyl-4-yl)-2-(6-propoxy-2-naphthyl)acetylene
1-(4'-Hexyloxybiphenyl-4-yl)-2-(6-propoxy-2-naphthyl)acetylene
1-(4'-Heptyloxybiphenyl-4-yl)-2-(6-propoxy-2-naphthyl)acetylene
1-(4'-Methylbiphenyl-4-yl)-2-(6-butoxy-2-naphthyl)acetylene
1-(4'-Ethylbiphenyl-4-yl)-2-(6-butoxy-2-naphthyl)acetylene
1-(4'-Propylbiphenyl-4-yl)-2-(6-butoxy-2-naphthyl)acetylene
1-(4'-Butylbiphenyl-4-yl)-2-(6-butoxy-2-naphthyl)acetylene
1-(4'-Pentylbiphenyl-4-yl)-2-(6-butoxy-2-naphthyl)acetylene
1-(4'-Hexylbiphenyl-4-yl)-2-(6-butoxy-2-naphthyl)acetylene
1-(4'-Heptylbiphenyl-4-yl)-2-(6-butoxy-2-naphthyl)acetylene
1-(4'-Octylbiphenyl-4-yl)-2-(6-butoxy-2-naphthyl)acetylene
1-(4'-Methoxybiphenyl-4-yl)-2-(6-butoxy-2-naphthyl)acetylene
1-(4'-Ethoxybiphenyl-4-yl)-2-(6-butoxy-2-naphthyl)acetylene
1-(4'-Propoxybiphenyl-4-yl)-2-(6-butoxy-2-naphthyl)acetylene
1-(4'-Butoxybiphenyl-4-yl)-2-(6-butoxy-2-naphthyl)acetylene
1-(4'-Pentyloxybiphenyl-4-yl)-2-(6-butoxy-2-naphthyl)acetylene
1-(4'-Hexyloxybiphenyl-4-yl)-2-(6-butoxy-2-naphthyl)acetylene
1-(4'-Heptyloxybiphenyl-4-yl)-2-(6-butoxy-2-naphthyl)acetylene
1-(4'-Methylbiphenyl-4-yl)-2-(6-pentyloxy-2-naphthyl)acetylene
1-(4'-Ethylbiphenyl-4-yl)-2-(6-pentyloxy-2-naphthyl)acetylene
1-(4'-Propylbiphenyl-4-yl)-2-(6-pentyloxy-2-naphthyl)acetylene
1-(4'-Butylbiphenyl-4-yl)-2-(6-pentyloxy-2-naphthyl)acetylene
1-(4'-Pentylbiphenyl-4-yl)-2-(6-pentyloxy-2-naphthyl)acetylene
1-(4'-Hexylbiphenyl-4-yl)-2-(6-pentyloxy-2-naphthyl)acetylene
1-(4'-Heptylbiphenyl-4-yl)-2-(6-pentyloxy-2-naphthyl)acetylene
1-(4'-Octylbiphenyl-4-yl)-2-(6-pentyloxy-2-naphthyl)acetylene
1-(4'-Methoxybiphenyl-4-yl)-2-(6-pentyloxy-2-naphthyl)acetylene
1-(4'-Ethoxybiphenyl-4-yl)-2-(6-pentyloxy-2-naphthyl)acetylene
1-(4'-Propoxybiphenyl-4-yl)-2-(6-pentyloxy-2-naphthyl)acetylene
1-(4'-Butoxybiphenyl-4-yl)-2-(6-pentyloxy-2-naphthyl)acetylene
1-(4'-Pentyloxybiphenyl-4-y1)-2 (6-pentyloxy-2-naphthyl)acetylene
1-(4'-Hexyloxybiphenyl-4-yl)-2-(6-pentyloxy-2-naphthyl)acetylene
1-(4'-Heptyloxybiphenyl-4-yl)-2-(6-pentyloxy-2-naphthyl)acetylene
1-(4'-Methylbiphenyl-4-yl)-2-(6-propyl-2-naphthyl)acetylene
1-(4'-Ethylbiphenyl-4-yl)-2-(6-propyl-2-naphthyl)acetylene
1-(4'-Propylbiphenyl-4-yl)-2-(6-propyl-2-naphthyl)acetylene
1-(4'-Butylbiphenyl-4-yl)-2-(6-propyl-2-naphthyl-)acetylene
1-(4'-Pentylbiphenyl-4-yl)-2-(6-propyl-2-naphthyl)acetylene
1-(4'-Hexylbiphenyl-4-yl)-2-(6-propyl-2-naphthyl)acetylene
1-(4'-Heptylbiphenyl-4-yl)-2-(6-propyl-2-naphthyl)acetylene
1-(4'-Octylbiphenyl-4-yl)-2-(6-propyl-2-naphthyl)acetylene
1-(4'-Methoxybiphenyl-4-yl)-2-(6-propyl-2-naphthyl)acetylene
1-(4'-Ethoxybiphenyl-4-yl)-2-(6-propyl-2-naphthyl)acetylene 1-(4'-Propoxybiphenyl-4-yl)-2-(6-propyl-2-naphthyl)acetylene
1-(4'-Butoxybiphenyl-4-yl)-2-(6-propyl-2-naphthyl)acetylene
1-(4'-Pentyloxybiphenyl-4-yl)-2-(6-propyl-2-naphthyl)acetylene
1-(4'-Hexyloxybiphenyl-4-yl)-2-(6-propyl-2-naphthyl)acetylene
1-(4'-Heptyloxybiphenyl-4-yl)-2-(6-propyl-2-naphthyl)acetylene
1-(4'-Methylbiphenyl-4-yl)-2-(6-pentyl-2-naphthyl)acetylene
1-(4'-Ethylbiphenyl-4-yl)-2-(6-pentyl-2-naphthyl)acetylene
1-(4'-Propylbiphenyl-4-yl)-2-(6-pentyl-2-naphthyl)acetylene
1-(4'-Butylbiphenyl-4-yl)-2-(6-pentyl-2-naphthyl)acetylene
1-(4'-Pentylbiphenyl-4-yl)-2-(6-pentyl-2-naphthyl)acetylene
1-(4'-Hexylbiphenyl-4-yl)-2-(6-pentyl-2-naphthyl)acetylene
1-(4'-Heptylbiphenyl-4-yl)-2-(6-pentyl-2-naphthyl)acetylene
1-(4'-Octylbiphenyl-4-yl)-2-(6-pentyl-2-naphthyl)acetylene
1-(4'-Methoxybiphenyl-4-yl)-2-(6-pentyl-2-naphthyl)acetylene
1-(4'-Ethoxybiphenyl-4-yl)-2-(6-pentyl-2-naphthyl)acetylene
1-(4'-Propoxybiphenyl-4-yl)-2-(6-pentyl-2-naphthyl)acetylene
1-(4'-Butoxybiphenyl-4-yl)-2-(6-pentyl-2-naphthyl)acetylene
1-(4'-Pentyloxybiphenyl-4-yl)-2-(6-pentyl-2-naphthyl)acetylene
1-(4'-Hexyloxybiphenyl-4-yl)-2-(6-pentyl-2-naphthyl)acetylene
1-(4'-Heptyloxybiphenyl-4-yl)-2-(6-pentyl-2-naphthyl)acetylene
1-[4-(trans-4-Methylcyclohexyl)phenyl]-2-(6-methoxy-2-naphthyl)acetylene
1-[4-(trans-4-Ethylcyclohexyl)phenyl]-2 (6-methoxy-2-naphthyl)acetylene
1-[4-(trans-4-Propylcyclohexyl)phenyl]-2-(6 methoxy-2-naphthyl)acetylene
1-[4-(trans-4-Butylcyclohexyl)phenyl]-2-(6-methoxy-2-naphthyl)acetylene
1-[4-(trans-4-Pentylcyclohexyl)phenyl]-2-(6-methoxy-2-naphthyl)acetylene
1-[4-(trans-4-Hexylcyclohexyl)phenyl]-2-(6-methoxy-2-naphthyl)acetylene
1-[4-(trans-4-Heptylcyclohexyl)phenyl]-2-(6-methoxy-2-naphthyl)acetylene
1-[4-(trans-4-Octylcyclohexyl)phenyl]-2-(6-methoxy-2-naphthyl)acetylene
1-[4-(trans-4-Nonylcyclohexyl)phenyl]-2-(6-methoxy-2-naphthyl)acetylene
1-[4-(trans-4-Methylcyclohexyl)phenyl]-2-(6-ethoxy-2-naphthyl)acetylene
1-[4-(trans-4-Ethylcyclohexyl)phenyl]-2-(6-ethoxy-2-naphthyl)acetylene
1-[4-(trans-4-Propylcyclohexyl)phenyl]-2-(6-ethoxy-2-naphthyl)acetylene
1-[4-(trans-4-Butylcyclohexyl)phenyl]-2-(6-ethoxy-2-naphthyl)acetylene
1-[4-(trans-4-Pentylcyclohexyl)phenyl]-2-(6-ethoxy-2-naphthyl)acetylene
1-[4-(trans-4-Hexylycyclohexyl)phenyl]-2-(6-ethoxy-2-naphthyl)acetylene
1-[4-(trans-4-Heptylcyclohexyl)phenyl]-2-(6-ethoxy-2-naphthyl)acetylene
1-[4-(trans-4-Octylcyclohexyl)phenyl]-2-(6-ethoxy-2-naphthyl)acetylene
1-[4-(trans-4-Nonylcyclohexyl)phenyl]-2-(6-ethoxy-2-naphthyl)acetylene
1-[4-(trans-4-Methylcyclohexyl)phenyl]-2-(6-propoxy-2-naphthylacetylene
1-[4-(trans-4-Ethylcyclohexyl)phenyl-]-2-(6-propoxy-2-naphthylacetylene
1-[4-(trans-4-Propylcyclohexyl)phenyl]-2-(6 propoxy-2-naphthylacetylene
1-[4-(trans-4-Butylcyclohexyl)phenyl]-2-(6-propoxy-2-naphthylacetylene
1-[4-(trans-4-Pentylcyclohexyl)phenyl]-2-(6-propoxy-2-naphthylacetylene
1-[4-(trans-4-Hexylcyclohexyl)phenyl]-2-(6-propoxy-2-naphthylacetylene
1-[4-(trans-4-Heptylcyclohexyl)phenyl]-2-(6-propoxy-2-naphthylacetylene
1-[4-(trans-4-Octylcyclohexyl)phenyl]-2-(6-propoxy-2-naphthylacetylene
1-[4-(trans-4-Nonylcyclohexyl)phenyl]-2-(6-propoxy-2-naphthylacetylene
1-[4-(trans-4-Methylcyclohexyl)phenyl]-2-(6-butoxy-2-naphthylacetylene
1-[4-(trans-4-Ethylcyclohexyl)phenyl]-2-(6-butoxy-2-naphthylacetylene
1-[4-(trans-4-Propylcyclohexyl)phenyl]-2-(6-butoxy-2-naphthylacetylene
1-[4-(trans-4-Butylcyclohexyl)phenyl]-2-(6-butoxy-2-naphthylacetylene
1-[4-(trans-4-Pentylcyclohexyl)phenyl]-2-(6-butoxy-2-naphthylacetylene
1-[4-(trans-4-Hexylcyclohexyl)phenyl]-2-(6-butoxy-2-naphthylacetylene
1-[4-(trans-4-Heptylcyclohexyl)phenyl]-2-(6-butoxy-2-naphthylacetylene
1-[4-(trans-4-Octylcyclohexyl)phenyl]-2-(6-butoxy-2-naphthylacetylene
1-[4-(trans-4-Nonylcyclohexyl)phenyl]-2-(6-butoxy-2-naphthyl)acetylene
1-[4-(trans-4-Methylcyclohexyl)phenyl]-2-(6-pentyloxy-2-naphthyl)acetylene
1-[4-(trans-4-Ethylcyclohexyl)phenyl]-2-(6-pentyloxy-2-naphthyl)acetylene
1-[4-(trans-4-Propylcyclohexyl)phenyl]-2-(6-pentyloxy-2-naphthyl)acetylene
1-[4-(trans-4-Butylcyclohexyl)phenyl]-2-(6-pentyloxy-2-naphthyl)acetylene
1-[4-(trans-4-Pentylcyclohexyl)phenyl]-2-(6-pentyloxy-2-naphthyl)acetylene
1-[4-(trans-4-Hexylcyclohexyl)phenyl]-2-(6-pentyloxy-2-naphthyl)acetylene
1-[4-(trans-4-Heptylcyclohexyl)phenyl]-2-(6-pentyloxy-2-naphthyl)acetylene
1-[4-(trans-4-Octylcyclohexyl)phenyl]-2-(6-pentyloxy-2-naphthyl)acetylene
1-[4-(trans-4-Nonylcyclohexyl)phenyl]-2-(6-pentyloxy-2-naphthyl)acetylene
1-[4-(trans-4-Methylcyclohexyl)phenyl]-2-(6-hexyloxy-2-naphthyl)acetylene
1-[4-(trans-4-Ethylcyclohexyl)phenyl]-2-(6-hexyloxy-2-naphthyl)acetylene
1-[4-(trans-4-Propylcyclohexyl)phenyl]-2-(6-hexyloxy-2-naphthyl)acetylene 1-[4-(trans-4-Butylcyclohexyl)phenyl]-2-(6-hexyloxy-2-naphthyl)acetylene
1-[4-(trans-4-Pentylcyclohexyl)phenyl]-2-(6-hexyloxy-2-naphthyl)acetylene
1-[4-(trans-4-Hexylcyclohexyl)phenyl]-2-(6-hexyloxy-2-naphthyl)acetylene
1-[4-(trans-4-Heptylcyclohexyl)phenyl]-2-(6-hexyloxy-2-naphthyl)acetylene
1-[4-(trans-4-Octylcyclohexyl)phenyl]-2-(6-hexyloxy-2-naphthyl)acetylene
1-[4-(trans-4-Nonylcyclohexyl)phenyl]-2-(6-hexyloxy-2-naphthyl)acetylene
1-[4-(trans-4-Methylcyclohexyl)phenyl]-2-(6 heptyloxy-2-naphthyl)acetylene
1-[4-(trans-4-Ethylcyclohexyl)phenyl]-2 (6-heptyloxy-2-naphthyl)acetylene
1-[4-(trans-4-Propylcyclohexyl)phenyl]-2-(6-heptyloxy-2-naphthyl)acetylene
1-[4-(trans-4-Butylcyclohexyl)phenyl]-2-(6-heptyloxy-2-naphthyl)acetylene
1-[4-(trans-4-Pentylcyclohexyl)phenyl]-2-(6-heptyloxy-2-naphthyl)acetylene
1-[4-(trans-4-Hexylcyclohexyl)phenyl]-2-(6-heptyloxy-2-naphthyl)acetylene
1-[4-(trans-4-Heptylcyclohexyl)phenyl]-2-(6-heptyloxy-2-naphthyl)acetylene
1-[4-(trans-4-Octylcyclohexyl)phenyl]-2-(6-heptyloxy-2-naphthyl)acetylene
1-[4-(trans-4-Nonylcyclohexyl)phenyl]-2-(6-heptyloxy-2-naphthyl)acetylene
1-[4-(trans-4-Methylcyclohexyl)phenyl]-2-(6-ethyl-2-naphthyl)acetylene
1-[4-(trans-4-Ethylcyclohexyl)phenyl]-2-(6-ethyl-2-naphthyl)acetylene
1-[4-(trans-4-Propylcyclohexyl)phenyl]-2-(6-ethyl-2-naphthyl)acetylene
1-[4-(trans-4-Butylcyclohexyl)phenyl]-2-(6-ethyl-2-naphthyl)acetylene
1-[4-(trans-4-Pentylcyclohexyl)phenyl]-2-(6-ethyl-2-naphthyl)acetylene
1-[4-(trans-4-Hexylcyclohexyl)phenyl]-2-(6-ethyl-2-naphthyl)acetylene
1-[4-(trans-4-Heptylcyclohexyl)phenyl]-2-(6-ethyl-2-naphthyl)acetylene
1-[4-(trans-4-Octylcyclohexyl)phenyl]-2-(6-ethyl-2-naphthyl)acetylene
1-[4-(trans-4-Nonylcyclohexyl)phenyl]-2-(6-ethyl-2-naphthyl)acetylene
1-[4-(trans-4-Methylcyclohexyl)phenyl]-2-(6-propyl-2-naphthyl)acetylene
1-[4-(trans-4-Ethylcyclohexyl)phenyl]-2-(6-propyl-2-naphthyl)acetylene
1-[4-(trans-4-Propylcyclohexyl)phenyl]-2-(6-propyl-2-naphthyl)acetylene
1-[4-(trans-4-Butylcyclohexyl)phenyl]-2-(6-propyl-2-naphthyl)acetylene
1-[4-(trans-4-Pentylcyclohexyl)phenyl]-2-(6-propyl-2-naphthyl)acetylene
1-[4-(trans-4-Hexylcyclohexyl)phenyl]-2-(6-propyl-2-naphthyl)acetylene
1-[4-(trans-4-Heptylcyclohexyl)phenyl]-2-(6-propyl-2-naphthyl)acetylene
1-[4-(trans-4-Octylcyclohexyl)phenyl]-2-(6-propyl-2-naphthyl)acetylene
1-[4-(trans-4-Nonylcyclohexyl)phenyl]-2-(6-propyl-2-naphthyl)acetylene
1-[4-(trans-4-Methylcyclohexyl)phenyl]-2-(6-butyl-2-naphthyl)acetylene
1-[4-(trans-4-Ethylcyclohexyl)phenyl]-2-(6-butyl-2-naphthyl)acetylene
1-[4-(trans-4-Propylcyclohexyl)phenyl]-2-(6-butyl-2-naphthyl)acetylene
1-[4-(trans-4-Butylcyclohexyl)phenyl]-2-(6-butyl-2-naphthyl)acetylene
1-[4-(trans-4-Pentylcyclohexyl)phenyl]-2-(6-butyl-2-naphthyl)acetylene
1-[4-(trans-4-Hexylcyclohexyl)phenyl]-2-(6-butyl-2-naphthyl)acetylene
1-[4-(trans-4-Heptylcyclohexyl)phenyl]-2-(6-butyl-2-naphthyl)acetylene
1-[4-(trans-4-Octylcyclohexyl)phenyl]2-(6-butyl-2-naphthyl)acetylene
1-[4-(trans-4-Nonylcyclohexyl)phenyl]-2-(6-butyl-2-naphthyl)acetylene
1-[4-(trans-4-Methylcyclohexyl)phenyl]-2-(6-pentyl-2-naphthyl)acetylene
1-[4-(trans-4-Ethylcyclohexyl)phenyl]-2-(6-pentyl-2-naphthyl)acetylene
1-[4-(trans-4-Propylcyclohexyl)phenyl]-2-(6-pentyl-2-naphthyl)acetylene
1-[4-(trans-4-Butylcyclohexyl)phenyl]-2-(6-pentyl-2-naphthyl)acetylene
1-[4-(trans-4-Pentylcyclohexyl)phenyl]-2-(6-pentyl-2-naphthyl)acetylene
1-[4-(trans-4-Hexylcyclohexyl)phenyl]-2-(6-pentyl-2-naphthyl)acetylene
1-[4-(trans-4-Heptylcyclohexyl)phenyl]-2-(6-pentyl-2-naphthyl)acetylene
1-[4-(trans-4-Octylcyclohexyl)phenyl]-2-(6-pentyl-2-naphthyl)acetylene
1-[4-(trans-4-Nonylcyclohexyl)phenyl]-2-(6-pentyl-2-naphthyl)acetylene
1-[4-(trans-4-Methylcyclohexyl)phenyl]-2-(6-hexyl-2-naphthyl)acetylene
1-[4(trans-4-Ethylcyclohexyl)phenyl]-2-(6-hexyl-2-naphthyl)acetylene
1-[4-(trans-4-Propylcyclohexyl)phenyl]-2-(6-hexyl-2-naphthyl)acetylene
1-[4-(trans-4-Butylcyclohexyl)phenyl]-2-(6-hexyl-2-naphthyl)acetylene
1-[4-(trans-4-Pentylcyclohexyl)phenyl]-2-(6-hexyl-2-naphthyl)acetylene
1-[4-(trans-4-Hexylcyclohexyl)phenyl]-2-(6-hexyl-2-naphthyl)acetylene
1-[4-(trans-4-Heptylcyclohexyl)phenyl]-2-(6-hexyl-2-naphthyl)acetylene
1-[4-(trans-4-Octylcyclohexyl)phenyl]-2-(6-hexyl-2-naphthyl)acetylene
1-[4-(trans-4-Nonylcyclohexyl)phenyl]-2-(6-hexyl-2-naphthyl)acetylene
1-[4-(trans-4-Methylcyclohexyl)phenyl]-2-(6-heptyl-2-naphthyl)acetylene
1-[4-(trans-4-Ethylcyclohexyl)phenyl]-2-(6-heptyl-2-naphthyl)acetylene
1-[4-(trans-4-Propylcyclohexyl)phenyl]-2-(6-heptyl-2-naphthyl)acetylene
1-[4-(trans-4-Butylcyclohexyl)phenyl]-2-(6-heptyl-2-naphthyl)acetylene
1-[4-(trans-4-Pentylcyclohexyl)phenyl]-2-(6-heptyl-2-naphthyl)acetylene
1-[4-(trans-4-Hexylcyclohexyl)phenyl]-2-(6-heptyl-2-naphthyl)acetylene
1-[4-(trans-4-Heptylcyclohexyl)phenyl]-2-(6-heptyl-2-naphthyl)acetylene
1-[4-(trans-4-Octylcyclohexyl)phenyl]-2-(6-heptyl-2-naphthyl)acetylene 1-[4-(trans-4-Nonylcyclohexyl)phenyl]-2-(6-heptyl-2-naphthyl)acetylene
1-[4-(trans-4-Methylcyclohexyl)phenyl]-2-(6-octyl-2-naphthyl)acetylene
1-[4-(trans-4-Ethylcyclohexyl)phenyl]-2-(6-octyl-2-naphthyl)acetylene
1-[4-(trans-4-Propylcyclohexyl)phenyl]-2-(6-octyl-2-naphthyl)acetylene
1-[4-(trans-4-Butylcyclohexyl)phenyl]-2-(6-octyl-2-naphthyl)acetylene
1-[4-(trans-4-Pentylcyclohexyl)phenyl]-2-(6-octyl-2-naphthyl)acetylene
1-[4-(trans-4-Hexylcyclohexyl)phenyl]-2-(6-octyl-2-naphthyl)acetylene
1-[4-(trans-4-Heptylcyclohexyl)phenyl]-2-(6-octyl-2-naphthyl)acetylene
1-[4-(trans 4-Octylcyclohexyl)phenyl]-2-(6 octyl-2-naphthyl)acetylene
1-[4-(trans-4-Nonylcyclohexyl)phenyl]-2-(6-octyl-2-naphthyl)acetylene The following examples relate to a liquid crystal phase according to the invention.

Example A

A liquid crystal phase consisting of
14% r-1-Cyan-cis-4-(trans-4-propylcyclohexyl)-1-propylcyclohexane,
20% 1-(trans-4-Propylcyclohexyl)-2-(4'-ethyl-2'-fluorobiphenyl-4-yl)ethane,
19% 1-(trans-4-Propylcyclohexyl)-2-(4'-pentyl-2'-fluorobiphenyl-4-yl)ethane,
17% 1-(trans-4-Pentylcyclohexyl)-2-(4'-ethyl-2'-fluorobiphenyl-4-yl-)ethane,
4% 4-(trans-4-Propylcyclohexyl)-2'-fluoro-4'-(trans-4-propylcyclohexyl)-biphenyl,
5% 4-(trans-4-Propylcyclohexyl)-2'-fluoro-4'-(trans-4-pentylcyclohexyl)-biphenyl,
7% 4-Butyl-4'-ethoxytolan,
7% 4-Pentyl-4'-methoxy-tolan and
7% 1-(4-Pentylphenyl)-2-(6-ethoxy-2-naphthyl)acetylene has a clear point of 101° and a $\Delta n$ of $+0.1675$.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A naphthyl)acetylene compound of the formula $$R^1-A^2-C\equiv C-A^3-R^2$$

in which
$R^1$ and $R^2$ are in each case independently of one another an alkyl group or polyfluoroalkyl group having up to 15 C atoms, in which one or more $CH_2$ groups or $CF_2$ groups respectively can also be replaced by —O—, —S—, —CO—, —O—CO—, —O—COO—, —CO—O—, —C≡C—, —CH=CH—, —CH-halogen- and —CHCN—, where two heteroatoms are not directly connected with one another, and one of the radicals $R^1$ and $R^2$ can also be halogen, CN or NCS; and $A^2$ and $A^3$ are in each case independently of one another
(a) 2,6-naphthylene radical,
(b) 1,2,3,4-tetrahydro-2,6-naphthylene radical,
(c) 1,4-phenylene radical, in which one or more CH groups can also be replaced by N,
(d) 1,4-cyclohexylene radical, or
(e) radical from the group comprising 1,4-cyclohexenylene, 1,4-cyclohexadienylene or 1,4-bicyclo(2.2.2)-octylene, where these radicals (a)–(e) can be substituted one or more times by halogen and/or cyano; with the proviso that at least one of the groups $A^2$ or $A^3$ is 2,6-naphthylene or 1,2,3,4-tetrahydro-2,6-naphthylene.

2. In a liquid crystal phase having at least two liquid crystal components, the improvement wherein at least one component is a naphthyl)acetylene compound according to claim 1.

3. In a liquid crystal display element comprising a liquid crystal phase, the improvement wherein the liquid crystal phase is one according to claim 2.

4. A compound according to claim 1 of the formulae Iaa to Iag:

| | |
|---|---|
| $R^1$—Nap—C≡C—Phe—$R^2$ | Iaa |
| $R^1$—Nap—C≡C—Cyc—$R^2$ | Iab |
| $R^1$—Nap—C≡C—Che—$R^2$ | Iac |
| $R^1$—Nap—C≡C—Cha—$R^2$ | Iad |
| $R^1$—Nap—C≡C—Pyd—$R^2$ | Iae |
| $R^1$—Nap—C≡C—Pyr—$R^2$ | Iaf |
| $R^1$—Tet—C≡C—Phe—$R^2$ | Iag, | wherein Nap is a 2,6-naphthylene group, Phe is a 1,4-phenylene group, Cyc is a 1,4-cyclohexylene group, Tet is a 1,2,3,4-tetrahydro-2,6-naphthylene group, Pyd is a pyridine-2,5-diyl group, Pyr is a pyrimidine-2,5-diyl group, Che is a 1,4-cyclohexylene group, and Cha is a 1,4-cyclohexadienylene group.

5. A compound according to claim 1 of the formulae 1 to 6:

| | |
|---|---|
| Alkyl—Nap—C≡C—Phe—Alkyl | 1 |
| Alkoxy—Nap—C≡C—Phe—Alkyl | 2 |
| Alkyl—Nap—C≡C—Cyc—Alkyl | 3 |
| Alkoxy—Nap—C≡C—Cyc—Alkyl | 4 |
| Alkoxy—Nap—C≡C—Pyd—Alkyl | 5 |
| Alkyl—Nap—C≡C—Pyr—Alkyl | 6, | wherein Nap is a 2,6-naphthylene group, Phe is a 1,4-phenylene group, Cyc is a 1,4-cyclohexylene group, Pyd is a pyridine-2,5-diyl group, and Pyr is a pyrimidine-2,5-diyl group.

6. A compound according to claim 1, wherein $R^1$ and $R^2$ independently have 2–10 C atoms.

7. A compound according to claim 1, wherein neither of the radicals $R^1$ and $R^2$ is halogen or CN.

8. A compound according to claim 11, wherein $R^1$ and $R^2$ together have 4–16 C atoms.

9. A compound according to claim 1, wherein one of $A^2$ or $A^3$ is 2,6-naphthylene.

10. A compound according to claim 1, wherein $A^2$ and $A^3$ are independently Cyc, Phe, Nap, Pyd, Tet, Pyr or Che, wherein Nap is a 2,6-naphthylene group, Phe is a 1,4-phenylene group, Cyc is a 1,4-cyclohexylene group, Tet is a 1,2,3,4-tetrahydro-2,6-naphthylene group, Pyd is a pyridine-2,5-diyl group, Pyr is a pyrimidine-2,5-diyl group, and Che is a 1,4-cyclohexylene group.

11. A compound according to claim 1, wherein $A^2$ or $A^3$ is a 1,2,3,4 tetrahydro-2,6-naphthylene group and is attached to the acetylene group at the 6-position.

12. A compound according to claim 1, wherein the 1,4-cyclohexylene radical has the following structure:

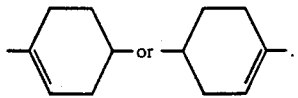

13. A compound according to claim 1, wherein the 1,4-cyclohexadienylene radical has the following structure:

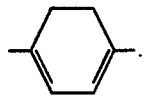

* * * * *